United States Patent [19]

Yamamoto et al.

[11] Patent Number: 4,660,983
[45] Date of Patent: Apr. 28, 1987

[54] APPARATUS FOR MEASURING REFLECTIVITIES OF RESONATOR FACETS OF SEMICONDUCTOR LASER

[75] Inventors: Osamu Yamamoto, Nara; Haruhisa Takiguchi, Osaka; Sadayoshi Matsui, Tenri, all of Japan

[73] Assignee: Sharp Kabushiki Kaisha, Osaka, Japan

[21] Appl. No.: 777,247

[22] Filed: Sep. 18, 1985

[30] Foreign Application Priority Data

Sep. 21, 1984 [JP] Japan ................. 59-199007

[51] Int. Cl.$^4$ ............................................. G01N 21/47
[52] U.S. Cl. .................................... 356/445; 356/124
[58] Field of Search ................. 356/124, 445; 250/206

[56] References Cited

U.S. PATENT DOCUMENTS 4,156,571  5/1979  Ljung .................................. 356/445

Primary Examiner—Eugene R. LaRoche
Assistant Examiner—Robert J. Pascal
Attorney, Agent, or Firm—Cohen, Pontani & Lieberman

[57] ABSTRACT

An apparatus for measuring the reflectivities of the resonator facets of a semiconductor laser when the facets are covered with a protective coating of dielectric material or the like, which comprises photodetector means for individually measuring the laser light powers from both facets of the resonator, reflector means for reflecting the laser light from one of the facets back to the laser, shutter means openable or closable at a position to block the laser light reflected from the reflector means, and photodetector means for measuring the power of the reflected laser light.

8 Claims, 3 Drawing Figures

APPARATUS FOR MEASURING REFLECTIVITIES OF RESONATOR FACETS OF SEMICONDUCTOR LASER

BACKGROUND OF THE INVENTION

1. Field of the Invention

The present invention relates to an apparatus for measuring the reflectivities of the resonator facets of a semiconductor laser when the facets are covered with a protective coating of dielectric material or the like.

2. Description of the Prior Art

Semiconductor lasers having varying light reflectivities have been developed wherein the facets of the resonator are covered with a protective coating of dielectric material or the like in order to prevent deterioration of the facets and to control the light reflectivities of the facets within predetermined values. Conventionally, the reflectivities of the resonator facets thus coated for protection are determined by measuring the optical output power from the front facet and the optical output power from the back facet and calculating the reflectivities from the following equation which represents the relation between these output powers and the reflectivities.

$$\frac{P1}{P2} = \frac{1-R1}{1-R2}\sqrt{\frac{R2}{R1}} \quad (1)$$

wherein
P1: light output power from one facet
R1: light reflectivity of one facet
P2: light output power from the other facet
R2: light reflectivity of the other facet
(As to Equation (1), see IEEE JOURNAL OF QUANTUM ELECTRONICS, Vol. QE-19, No. 3, March 1983.)

With this method of calculation, however, it is impossible to determine the reflectivity of one facet, i.e., one of R1 and R2, unless the reflectivity of the other facet is known. Accordingly, it is common practice to make one of the resonator facets assume the state of a cleaved plane having a known reflectivity, to form a protective coating only over the other facet to provide an altered reflectivity and to calculate the reflectivity of the coated facet from Equation (1). In the case where both facets are provided with a protective coating, a monitoring semiconductor laser is used in which one facet is in the form of a cleaved plane as described above and the other facet is provided with a protective coating under the same condition as the coating concerned, and the reflectivity of the coated facet is determined from Equation (1). It is therefore impossible to directly measure the facet reflectivities of individual semiconductor lasers and to check the variations involved in the manufacturing process.

SUMMARY OF THE INVENTION

The present invention provides an apparatus for measuring the reflectivities of the resonator facets of a semiconductor laser comprising photodetector means for individually measuring the laser light powers from both resonator facets of the laser, reflector means for reflecting the laser light from one of the facets back to the laser, shutter means selectively openable for allowing the laser light reflected from the reflector means to pass towards the laser or selectively closable for blocking the laser light reflected from the reflector means, and photodetector means for measuring the power of the reflected laser light.

When the light output from the resonator front facet of a semiconductor laser is partly fed-back to the light emitting facet, the amount of fed-back light or light feedback has a definite functional relation with the front facet light output as well as the back facet light output as will be described below with reference to FIG. 2. The resonator facets of the laser are indicated at f1 and f2, and it is assumed that the reflectivities of the facets f1 and f2 are R1 and R2, respectively. Further suppose the light output power from f1 is P1, the light output power from f2 is P2, and the power of a portion of output light from f1 as reflected from an external reflector M is rP1 ($0 \leq r \leq 1$). The light of power rP1 is to be fed back into the resonator through the facet f1 of the laser. Further, the light output powers in the resonator in the direction of incidence and the direction of reflection at f1 are P1' and P1'', respectively, the light output powers in the direction of incidence and the direction of reflection at f2 are P2' and P2'', respectively, and the gain of the resonator is A. The relations between these values are represented by the following equations.

$$P1 = (1-R1)P1' \quad (2)$$

$$P1'' = \{\sqrt{R1} + (1-R1)\sqrt{r}\}^2 P1' \quad (3)$$

$$P2 = (1-R2)P2' \quad (4)$$

$$P2'' = R2P2' \quad (5)$$

$$P2' = AP1'' \quad (6)$$

$$P1' = AP2'' \quad (7)$$

Equations (2) to (7) give the following equation.

$$\frac{P1}{P2} = \frac{1-R1}{1-R2} \cdot \frac{\sqrt{R2}}{\sqrt{R1}+(1-R1)\sqrt{r}} \quad (8)$$

Thus, when r, R1 and R2 are given, the ratio of P1 to P2 can be determined. Further when there is no light feedback, i.e., when r=0, the ratio is given by Equation (1).

When the amount of light feedback is rP1, the ratio of the front facet light output power P1(r) to the back facet light output P2(r) is Xr, and when there is no light feedback, the front facet light output power P1 and the back facet light output power P2 are represented by the ratio of X0. Xr, X0 and the ratio of X0 to Xr are given by:

$$X0 = \frac{P1}{P2} = \frac{1-R1}{1-R2}\sqrt{\frac{R2}{R1}} \quad (r=0) \quad (9)$$

$$Xr = \frac{P1(r)}{P2(r)} = \frac{1-R}{1-R2} \cdot \frac{\sqrt{R2}}{\sqrt{R1}+(1-R1)\sqrt{r}} \quad (10)$$

$$\frac{Xr}{X0} = \frac{\sqrt{R1}}{\sqrt{R1}+(1+R1)\sqrt{r}} \quad (11)$$

Thus, R1 can be determined when the ratio r of the amount of light feedback to the amount of emitted light, the ratio X0 of the front facet light output power to the back facet light output power in the absence of fed-back light, and the ratio Xr of the front facet light output power to the back facet light output power in the presence of fed-back light are determined. Next, R2 can be determined from Equation (1).

Accordingly, the main object of the present invention is to provide an apparatus for measuring the reflectivities of the resonator facets of a semiconductor laser by utilizing feedback of the light emitted by the laser even when the facets are provided with a protective coating.

DESCRIPTION OF THE PREFERRED EMBODIMENTS

Figure 1:
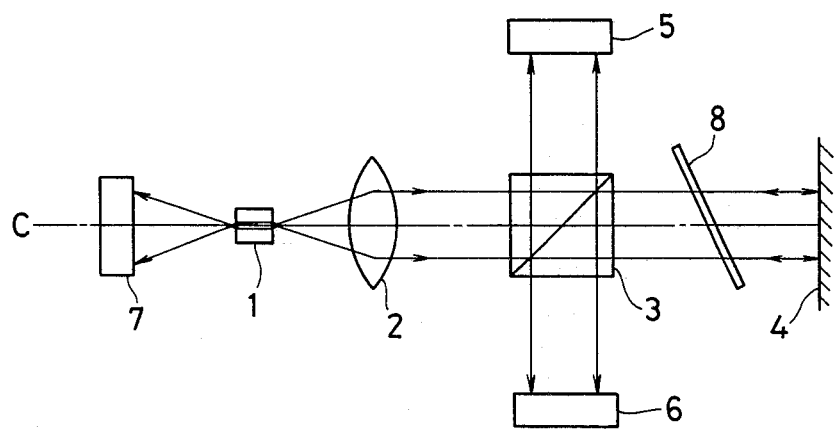
FIG. 1 is a diagram showing the construction of an apparatus for measuring the facet reflectivities of a semiconductor laser embodying the invention.
Figure 2:
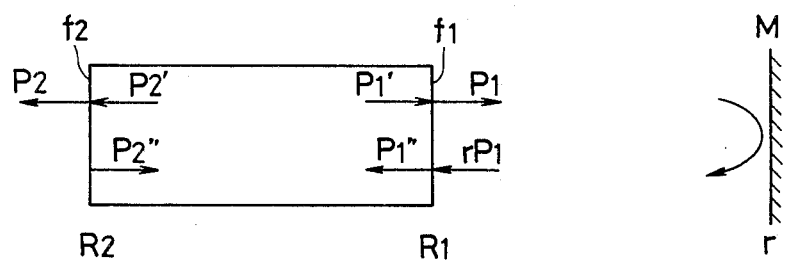
FIG. 2 is a diagram illustrating the basic principle of the invention.

FIG. 1 is a diagram showing the construction of an apparatus embodying the invention for measuring the facet reflectivities of a semiconductor laser 1.

The laser oscillation resonator of the laser 1 has opposite facets which are provided with a protective coating of a dielectric material such as $SiO_2$ or $Al_2O_3$. Arranged toward the direction of emergence of the laser light from one of the facets (front facet) are a collimator lens 2, a beam splitter 3 for dividing the light through the lens 2 in two directions at a right angle to each other, and a reflector 4 for reflecting the laser light. Photodetectors 5 and 6, such as photodiodes or phototransistors, are so positioned as to receive the laser beams divided by the beam splitter 3. Disposed adjacent the other facet (back facet) of the laser 1 is a photodetector 7 on which the laser light from the back facet impinges. A shutter 8 for blocking the reflected laser light is interposed between the beam splitter 3 and the reflector 4. The photodetector 7, the semiconductor laser 1, the collimator lens 2 and the beam splitter 3 are aligned on the optical axis C shown.

The laser light from the back facet of the laser 1 impinges on the photodetector 7, whereby the output power of the light is measured. The laser light from the front facet is made into a beam of parallel rays upon passage through the collimator lens 2 and then divided in two directions by the beam splitter 3. The laser light deflected by the beam splitter 3 in a direction perpendicular to the optical axis C strikes the photodetector 5, whereby the light output power from the front facet is measured. The laser light traveling straight along the optical axis C from the beam splitter 3 is incident on the surface of the reflector 4 perpendicular thereto, and the reflected light travels in the reverse direction along the axis C and impinges on the beam splitter 3, by which the reflected light is divided into a beam along the optical axis and a beam toward a direction at a right angle with the optical axis C. The latter beam strikes the photodetector 6, whereby the power thereof is measured. The light traveling along the axis C passes through the collimator lens 2 and is fed back into the laser 1 through the facet, thus providing a complex resonator.

With the above arrangement, the shutter 8 is closed to block the reflected light, and the ratio of X0 of the front facet output power P1 to the back facet output power P2 is determined when there is no light fed back to the laser 1, based on the amounts of light incident on the photodetectors 5 and 7. Next, the shutter 8 is opened to cause the reflector 3 to reflect the laser light and then feed back the light to the laser 1, and the ratio Xr of the front facet output power P1(r) and the back facet output power P2(r) is determined. At the same time, the ratio of the amount of light feedback to the amount of light emitted by the front facet is measured by the photodetectors 5 and 6. The front facet reflectivity R1 is obtained by substituting the measurements X0, Xr and r in Equation (11). R2 can then be obtained from Equation (1).

Figure 3:
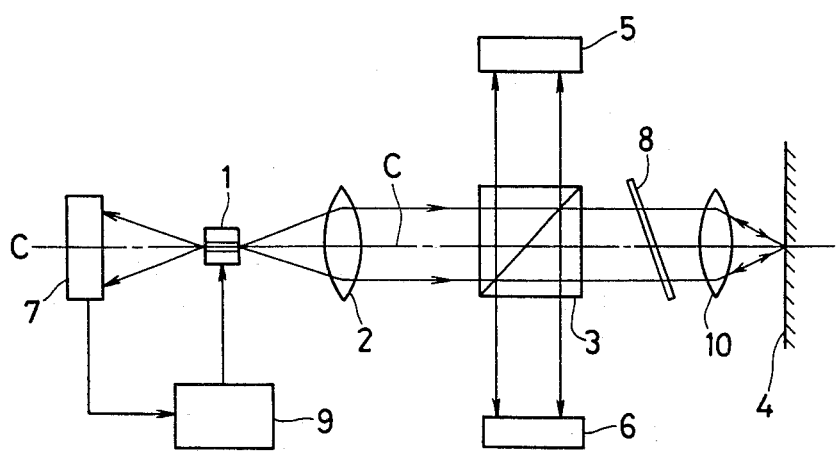
FIG. 3 is a diagram showing the construction of another embodiment of the invention.

FIG. 3 shows the construction of another apparatus embodying the invention for measuring the facet reflectivities of a semiconductor laser.

This embodiment has the same construction as the one shown in FIG. 1 with respect to the laser 1, collimator lens 2, beam splitter 3 and photodetector 5, 6. The laser light from the back facet of the laser 1 impinges on a photodetector 7, the resulting detecting signal of which is fed to an APC (automatic power control) circuit 9. The drive current for the semiconductor laser 1 is controlled by the output signal from the APC circuit 9. The output laser light passing through the beam splitter 3 and traveling along the optical axis C is converged upon passage through a condenser lens 10 and strikes a reflector 4 in the form of a spot. The reflected light passes through the condenser lens 10 in the reverse direction, travels along the optical axis C and is fed back to the laser 1. The output power of the laser 1 is detected by the photodetector 7, and the variation of the output power is fed back to the drive system through the APC circuit 9, whereby the laser 1 is so driven that the power thereof will be constant at all times. In this case, Equations (9) and (10) are expressed as follows.

$$X0 = \frac{P1}{P2} = \frac{1 - R1}{1 - R2} \cdot \sqrt{\frac{R2}{R1}} \quad (9)'$$

$$Xr = \frac{P1(r)}{P2(r)} = \frac{1 - R1}{1 - R2} \cdot \frac{\sqrt{R2}}{\sqrt{R1} + (1 - R1)\sqrt{r}} \quad (10)'$$

Equation (11) is expressed as follows.

$$\frac{P1(r)}{P1} = \frac{\sqrt{R1}}{\sqrt{R1} + (1 - R1)\sqrt{r}} \quad (11)'$$

Thus, R1 can be easily calculated merely with use of the detection signal of the photodetector 5.

Besides the facet reflectivities, variations in the facet reflectivities of the semiconductor laser 1 can also be measured.

According to the invention described above in detail, the light reflectivities of the opposite resonator facets of semiconductor lasers can be directly measured with high precision, while the present apparatus is usable also for checking optical elements, for example, for variations of light reflectivity. Accordingly, the present invention is expected to contribute to improved yields, improved qualities, etc. in the manufacturing process of semiconductor lasers.

What is claimed is:

1. An apparatus for measuring the reflectivities of the resonator facets of a semiconductor laser comprising:

photodetector means for individually measuring the laser light powers from both facets of the resonator;

reflector means for reflecting the laser light from one of the facets back to the laser;

shutter means selectively openable for allowing the laser light reflected from the reflector means to pass towards the laser or selectively closable for blocking the laser light reflected from the reflector means; and photodetector means for measuring the power of the reflected laser light.

2. An apparatus as defined in claim 1, wherein each of the photodetector means is a photodiode.

3. The apparatus as defined in claim 1, wherein each of the photodetector means is a phototransistor.

4. The apparatus as defined in claim 1, further comprising means for producing parallel rays of laser light positioned adjacent the laser in the path the laser light exiting therefrom.

5. The apparatus as defined in claim 4, further comprising beam splitting means positioned in the path of the laser light between the laser and the photodetector means for splitting and deflecting laser light towards the photodetector means and towards the reflector means.

6. The apparatus as defined in claim 5, wherein the photodetector means include a first photodetector for measuring the light output power from the front facet of the laser;

a second photodetector positioned in the laser light being reflected by the reflector means for measuring the amount reflected thereby; and a third photodetector positioned in the path of the laser light exiting from the second facet of the laser for measuring the output power thereof.

7. The apparatus as defined in claim 6, wherein the third photodetector, the laser, the means for producing parallel rays of light and the beam splitting means are positioned along the optical axis of the laser.

8. The apparatus as defined in claim 7, wherein the shutter means are positioned between the beam splitting means and the reflector means.

* * * * *